(12) United States Patent
Kim

(10) Patent No.: US 11,185,388 B2
(45) Date of Patent: Nov. 30, 2021

(54) SURGICAL VIDEO PRODUCTION SYSTEM AND SURGICAL VIDEO PRODUCTION METHOD

(71) Applicant: 3D MediVision Inc., Seoul (KR)

(72) Inventor: Kijin Kim, Seongnam-si (KR)

(73) Assignee: 3D MediVision Inc., Seoul (KR)

( * ) Notice: Subject to any disclaimer, the term of this patent is extended or adjusted under 35 U.S.C. 154(b) by 0 days.

(21) Appl. No.: 16/310,869

(22) PCT Filed: Dec. 10, 2018

(86) PCT No.: PCT/KR2018/015623
§ 371 (c)(1),
(2) Date: Dec. 18, 2018

(87) PCT Pub. No.: WO2020/116701
PCT Pub. Date: Jun. 11, 2020

(65) Prior Publication Data
US 2021/0282892 A1 Sep. 16, 2021

(30) Foreign Application Priority Data

Dec. 5, 2018 (KR) .......................... 10-2018-0155238

(51) Int. Cl.
*A61B 90/90* (2016.01)
*A61B 90/00* (2016.01)
(Continued)

(52) U.S. Cl.
CPC ............ *A61B 90/90* (2016.02); *A61B 90/361* (2016.02); *A61B 90/39* (2016.02); *G06T 7/13* (2017.01);
(Continued)

(58) Field of Classification Search
CPC combination set(s) only.
See application file for complete search history.

(56) References Cited

FOREIGN PATENT DOCUMENTS

| JP | 2011-036371 | 2/2011 |
|---|---|---|
| JP | 2011-036371 A | 2/2011 |

(Continued)

OTHER PUBLICATIONS

KIPO, International Search Report of Application No. PCT/KR2018/015623, dated Aug. 26, 2019.
(Continued)

*Primary Examiner* — Scott Luan
(74) *Attorney, Agent, or Firm* — Studebaker & Brackett PC

(57) ABSTRACT

A surgical video production system consists of: an input part which records time codes in a moving, and inputs a focal distance of a lens and information of surgical tools, a recognition part which generates recognition information by recognizing the surgical tools, organs, tissue, and objects in the moving image, identifies unfocused video and shaky video, indicates markers corresponding to a first time code and a last time code of each of the unfocused video and the shaky moving image, and indicates the markers corresponding to the first time code and the last time code of the moving image corresponding to the event; an editing part, which deletes a part of the moving image using the markers or separates a moving image according to the event to generate an edited image; and a transformation part which transforms an edited image into a stereoscopic image.

12 Claims, 13 Drawing Sheets

(51) Int. Cl.
 G06T 7/168 (2017.01)
 G06T 7/13 (2017.01)
(52) U.S. Cl.
 CPC .... *G06T 7/168* (2017.01); *G06T 2207/30004* (2013.01)

(56) References Cited

FOREIGN PATENT DOCUMENTS

| KR | 10-1175065 | 10/2012 |
|---|---|---|
| KR | 10-1175065 B1 | 10/2012 |
| KR | 10-1670187 | 10/2016 |
| KR | 10-1670187 B1 | 10/2016 |
| KR | 10-2016-0136833 | 11/2016 |
| KR | 10-2016-0136833 A | 11/2016 |
| KR | 10-2017-0114700 | 10/2017 |
| KR | 10-2017-0114700 A | 10/2017 |
| KR | 10-1880246 | 7/2018 |
| KR | 10-1880246 B1 | 7/2018 |

OTHER PUBLICATIONS

KIPO, Written Opinion of the International Searching Authority of Application No. PCT/KR2018/015623, dated Aug. 26, 2019.
KIPO, Notification of Transmittal of the International Search Report and the Written Opinion of the International Searching Authority of Application No. PCT/KR2018/015623, dated Aug. 26, 2019.

SURGICAL VIDEO PRODUCTION SYSTEM AND SURGICAL VIDEO PRODUCTION METHOD

CROSS-REFERENCE TO RELATED APPLICATION

The present application is based on, and claims priority from, Korean Patent Application No. 10-2018-0155238, filed on Dec. 5, 2018, the disclosure of which is hereby incorporated by reference herein in its entirety.

TECHNICAL FIELD

The present invention relates to a surgical video production system and a surgical video production method, and more particularly, to a stereoscopic video production system for a surgical operation using a microscope and a video production method thereof.

BACKGROUND

In general, a medical surgical microscope is a type of medical device that allows an operator to operate inside of a human body that can not be easily identified. A surgical microscope is provided with a monitor for monitoring a surgeon's surgery. At this time, since the image displayed on the monitor is simply displayed as a two-dimensional image, it is difficult to accurately observe and check the surgical field with such an image.

For this reason, in order to produce a three-dimensional image, there is a growing need for a system for converting a captured image into a stereoscopic image. However, because surgical tools included in a surgical video and techniques for recognizing various human organs rely on human thought, there is a limit that various situations cannot be appropriately responded to.

In addition, as recognition of such surgical tools and organs is based on human cognitive ability, it is difficult to learn a large number of surgical tools and organs, there is a problem that the accuracy of recognition is low, and there is a difficulty in providing objective and accurate recognition performance of small devices and organs.

DISCLOSURE

Technical Problem

The present invention is made to overcome the above-mentioned problems, and has the purpose of providing a surgical video production system and a surgical video production method capable of transforming a 2D microscopic surgical video to a stereoscopic video by accurately recognizing and editing surgical tools and various human organs included in the 2D microscopic surgical video.

Technical Solution

The present embodiment of the invention provides a surgical video production system consisting of: an input part which records time codes in a moving image photographed by a camera mounted on a surgical microscope, and inputs a focal distance of a lens of the camera and information of surgical tools; a recognition part which generates recognition information by recognizing the surgical tools, surgical fields, organs, tissue, and objects in the moving image, identifies unfocused video and shaky video among video using the recognition information, indicates markers corresponding to a first time code and a last time code of each unfocused video and shaky moving image, and indicates the markers corresponding to the first time code and the last time code of the video corresponding to an event by recognizing an event occurring during surgery using the recognition information; 3) an editing part, which deletes a part of the moving image using the markers or separates a moving image according to the event to generate an edited image; and 4) a transformation part which transforms the edited image into a stereoscopic image.

In addition, the recognition information according to the present embodiment includes an edge of a surgical tool, an edge of a surgical field, an edge of an organ, and an edge of tissue.

The recognition part according to the present embodiment recognizes a region of the surgical field which includes an edge of the surgical tool as a first surgical field, and when the first surgical field disappears within a first time, an appropriate moving image is determined as a first shaky moving image.

The recognition part according to the present embodiment also recognizes movement of the end of the surgical tool, senses an end region constituted by the movement path of the end during a reference time, and recognizes the field which includes the end region as a second surgical field. Further, when the second surgical field disappears within a second time, the moving image is recognized as a second shaky moving image.

The recognition part according to the present embodiment compares a focal distance measured in the moving image with an input measured distance, and when the measured focal distance and the input focal distance are not within a critical range, the appropriate moving image is identified as the unfocused one.

The event according to the present embodiment includes a bleeding event, a blind spot event, a first extraction event, a hemostasis event, a drilling event, and a second extraction event, and the object includes blood. In addition, when a ratio of an area of the blood to an area of the tissue at the second surgical field exceeds a first reference value, the recognition part recognizes the corresponding moving image as the bleeding event.

The object according to the present embodiment includes a hand, and the recognition part recognizes a corresponding motion image as the blind spot event when the area of the hand exceeds a second reference value at the second surgical field.

The recognition part according to the present embodiment recognizes the corresponding moving image as the second extraction event when a part of the recognized organs disappears within a third time.

The surgical tool according to the present embodiment includes bipolar forceps, a burr drill, forceps, and a cutter. The recognition part recognizes the moving image including the bipolar forceps as the hemostatic event, the moving image including the burr drill as the drilling event, and the moving image including the forceps and the cutter as the hemostatic event, respectively.

The recognition information according to the present embodiment is generated using a moving image analysis algorithm or a deep learning technique.

The edge of the surgical tool, the edge of the surgical field, the edge of the organ, and the edge of the tissue according to the present embodiment are identified using at least one of Sobel, Prewitt, Roberts, Compass, Laplacian, Laplacian of Gaussian (LoG), and Canny methods.

In addition, the transformed stereoscopic image according to the present embodiment is a stereoscopic surgery moving image for educating surgeons.

Advantageous Effects

The present invention has an effect of providing a surgical video production system and a surgical video production method which can correctly recognize and edit surgical tools and various human organs included in a photographed microscopic 2D moving image, and transform it into a stereoscopic image.

BRIEF DESCRIPTION ON DRAWINGS

DETAILED DESCRIPTION OF THE EMBODIMENTS

Figure 1:
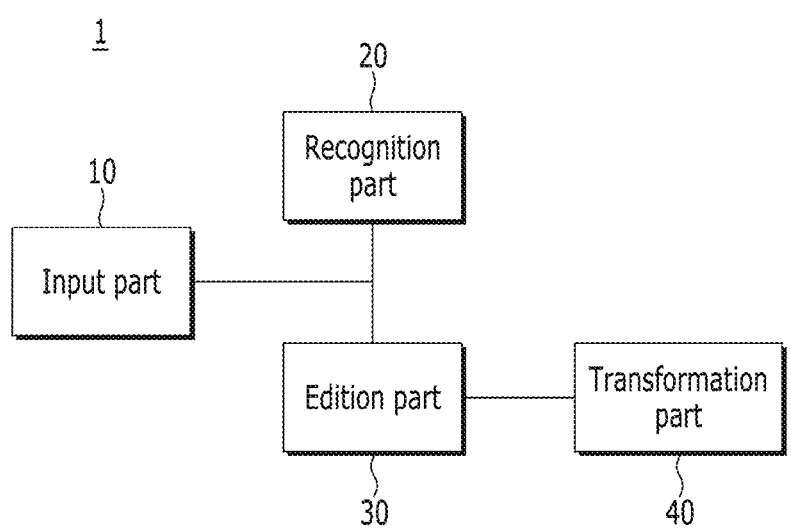
FIG. 1 is a block diagram illustrating the surgical video production system according to the present embodiment.

Hereinafter, the present embodiment of the invention is explained in detail by referring to the accompanying figures, wherein same or similar reference numerals refer to the same or similar elements throughout the figures, and repeated explanation may be omitted. It should be understood that the attached figures are intended only to easily understand the present embodiment disclosed in this patent specification, and the technical idea of the invention is not limited to the disclosed embodiments, but, on the contrary, should be regarded to cover various modifications, equivalents, and alternatives included within the idea and scope of the invention FIG. 1 is a block diagram which illustrates a configuration of a surgical video production system according to the present embodiment.

Referring to FIG. 1, a surgical video production system (1) according to the present embodiment includes an input part (10), a recognition part (20), an editing part (30), and a transformation part (40). The stereoscopic moving image generated by the surgical video production system (1) is an educational stereoscopic video for educating surgeons in medical schools or general hospitals.

The microscope operation video (hereinafter referred to as the moving image) obtained by a camera mounted on a surgical microscope, focal distance (hereinafter referred to as focal distance) information of a camera lens, and tool information of a surgical tool (hereinafter referred to as the tool) are input into the input part (10).

Specifically, a 2D camera attached to a surgical microscope takes moving images which are seen by the operating surgeon through a surgical microscope. There is a specific distance between the surgical field and the microscope for each operation type, and a lens having a focal distance corresponding to this specific distance is attached to a camera in order to take the moving image. Accordingly, the focal distance can have a unique value for each operation type. In addition, the tool information includes names, shapes, materials, precautions for use, and specific features of various surgical tools used in surgery.

The input part (10) records the time code of all or parts of the obtained moving images, and performs the first editing step where patient information, disease name, operation procedure, tools used, and focal distance of the lens mounted on the camera in relation to the operation of obtained moving images are input.

The recognition part (20) generates recognition information including the results of recognizing surgical tools, surgical fields, organs, tissue, and objects in the moving image. The recognition part (20) identifies shaky moving images and non-focused moving images, and indicates markers corresponding to the first time code and the last time code of the identified moving image using the recognition information. Also, the recognition part (20) recognizes events (for example, bleeding, hemostasis, blind spots, extraction, etc.) which occur during the operation using the recognition information. In addition, the recognition part (20) indicates the markers corresponding to the first time code and the last time code of the recognized moving image using the recognition information.

The editing part (30) recognizes the indicated marker and performs second editing using the marker, deletes the shaky and unfocused moving images, separates the moving image according to the event, or indicates the tool information of the currently displayed tool on the moving image, and creates the edited moving images.

The transformation part (40) transforms an edited moving image into a stereoscopic image. In such a transformation, a virtual reality (VR) video, a side by side video, or a top and bottom video are created in consideration of the type of the device by which the video is played.

Specifically, the transformation part (40) can transform the second editing completed moving image into a virtual reality moving image having resolution of 3840×1080p (1920×1080 respectively) or 1920×1080p (960×1080 respectively), and into a side by side moving image having resolution of 1920×1080p (960×1080p respectively) or 3840×2160p (1920×2160 respectively), and into a top and bottom moving image having a resolution of 1920×1080p (1920×590 respectively) or 3840×2160p (3840×1080 respectively).

Hereinafter, the operation of the recognition part (20) is described in detail with reference to FIG. 2 to FIG. 9.

The recognition part (20) can apply the motion analysis algorithm to the motion image to recognize the organ, tissue, object (a specific part of blood or tissue), and tool, and generate the recognition information. The video analysis algorithm is only an example, and the organ, tissue, object, and tool can be identified by using at least one of anatomical information of organs or tissue, tool information, edge information, color information, intensity change information, surface color spectrum change information, and moving image characteristic information. In addition, the recognition part (20) can apply a deep learning technology to a moving image in order to identify and recognize the organ, tissue, tool, and object, but the present invention is not limited thereto.

In addition, the recognition part (20) can recognize the edge of an organ, the edge of tissue, the edge of an object, and the tool edge, and generate the recognition information by using at least one of Sobel, Prewitt, Roberts, Compass, Laplacian, Laplacian of Gaussian (LoG), and Canny methods.

Figure 2:
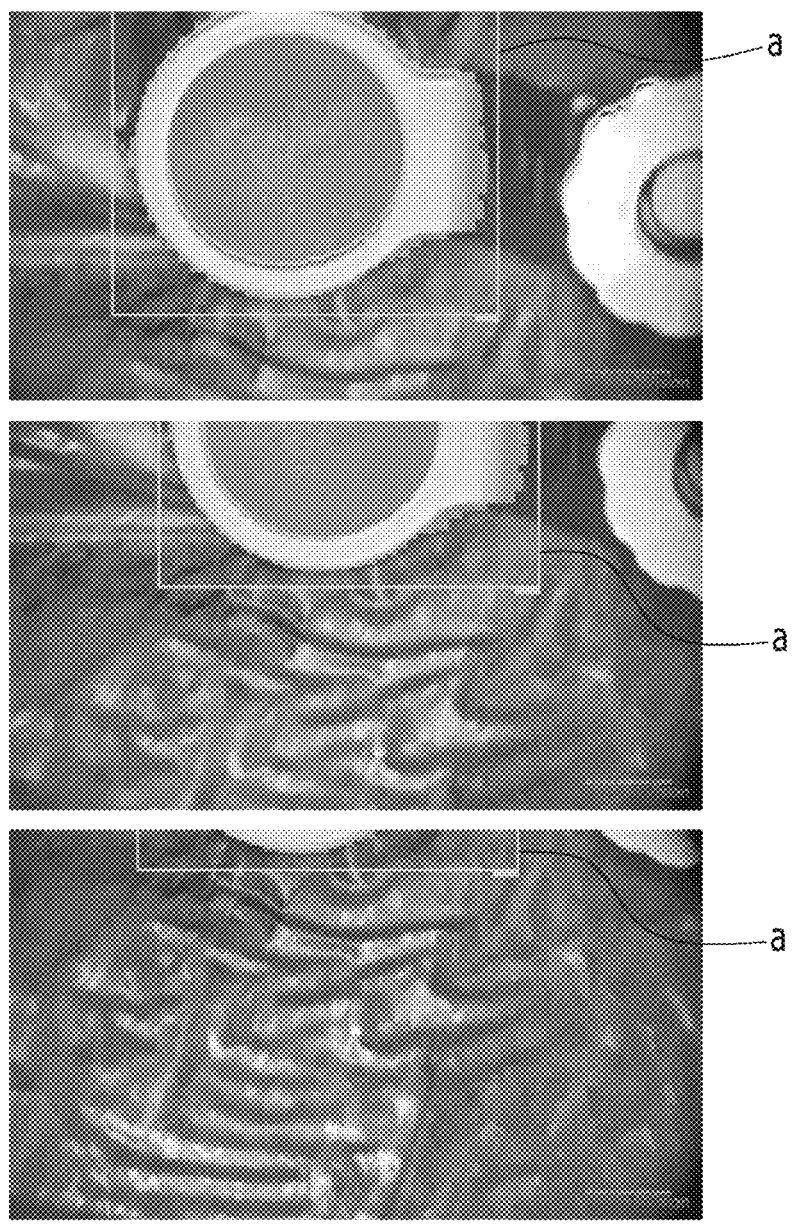
FIG. 2 shows examples in which the image recognition part according to the present embodiment recognizes the first surgical field.
Figure 3:
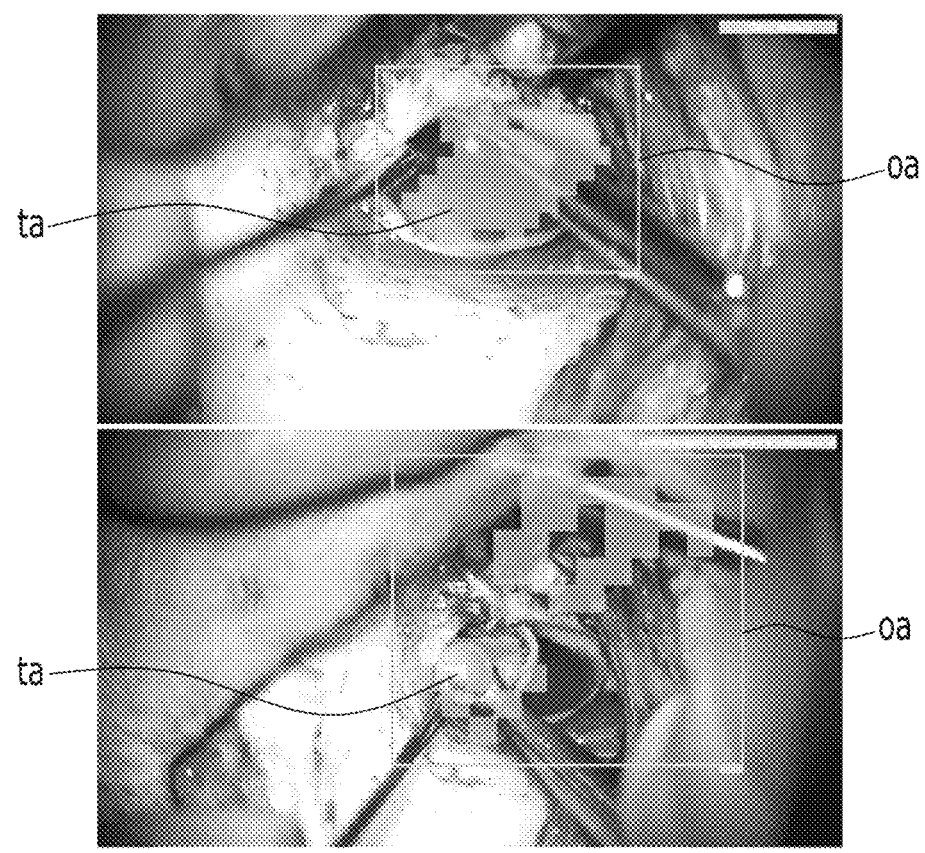
FIG. 3 shows examples in which the image recognition part according to the present embodiment recognizes the second surgical field.
Figure 4A:
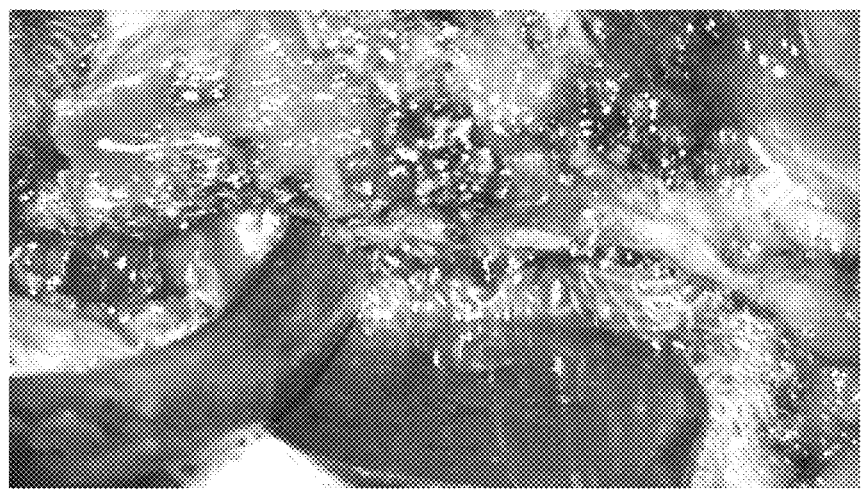
FIG. 4a and FIG. 4b show examples in which the image recognition part according to the present embodiment recognizes bleeding events.
Figure 4B:
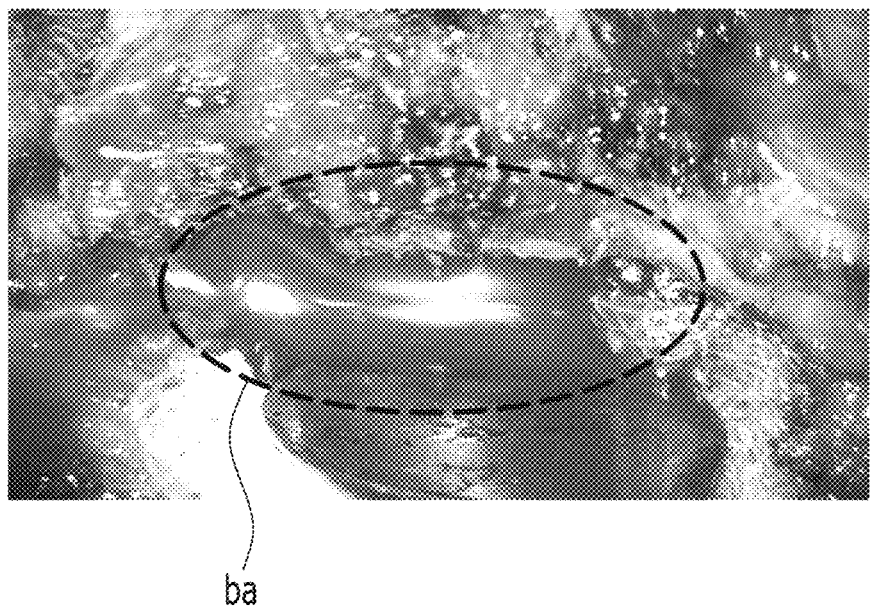
Figure 5A:
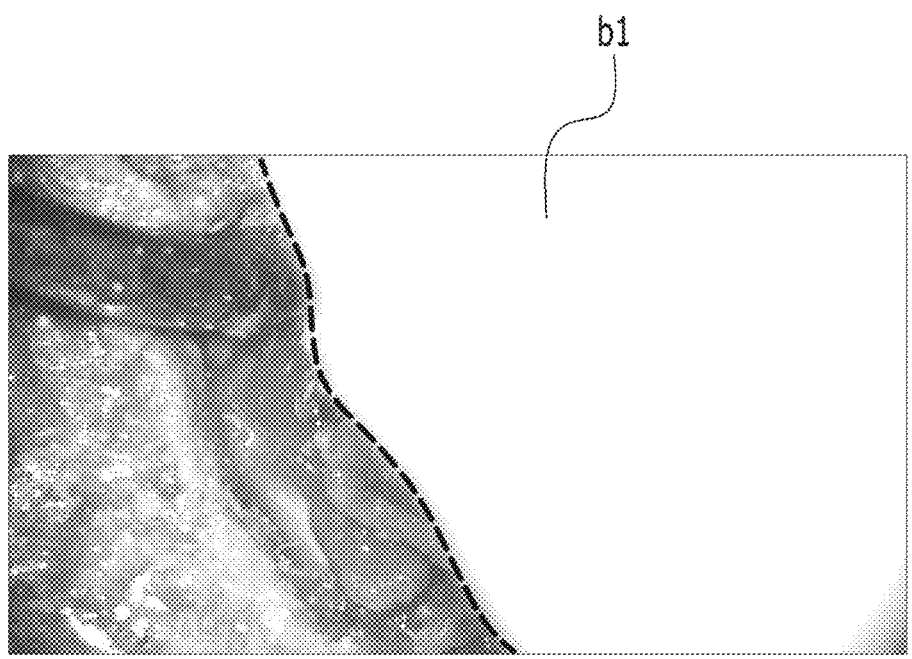
FIG. 5a and FIG. 5b show examples in which the image recognition part according to the present embodiment recognizes blind spot events.
Figure 5B:
Figure 6A:
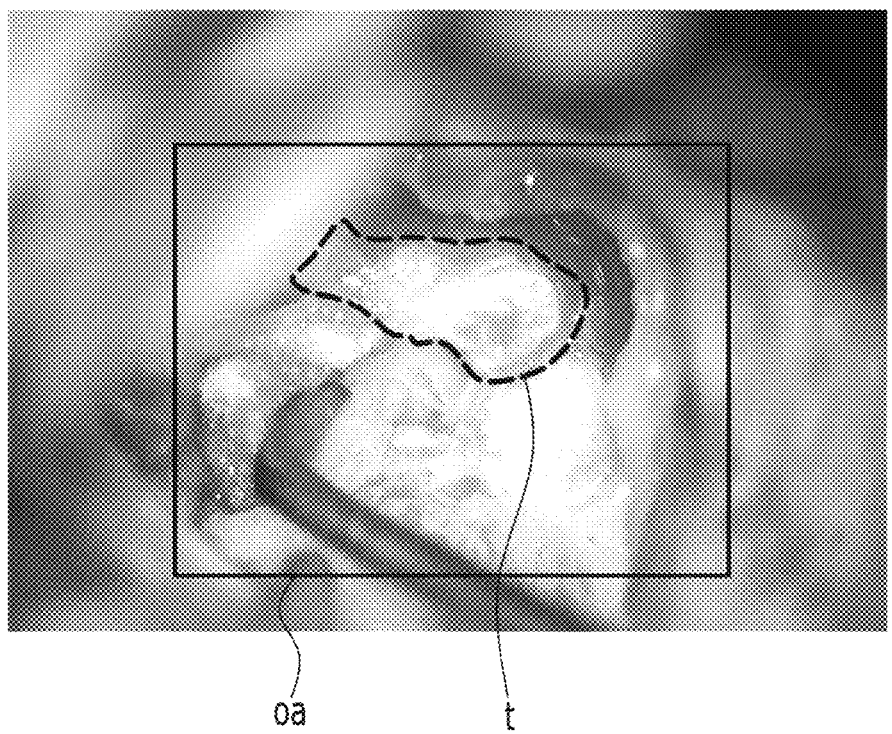
FIG. 6a and FIG. 6b are views illustrating examples in which the image recognition part according to the present embodiment recognizes the first extraction event.
Figure 6B:
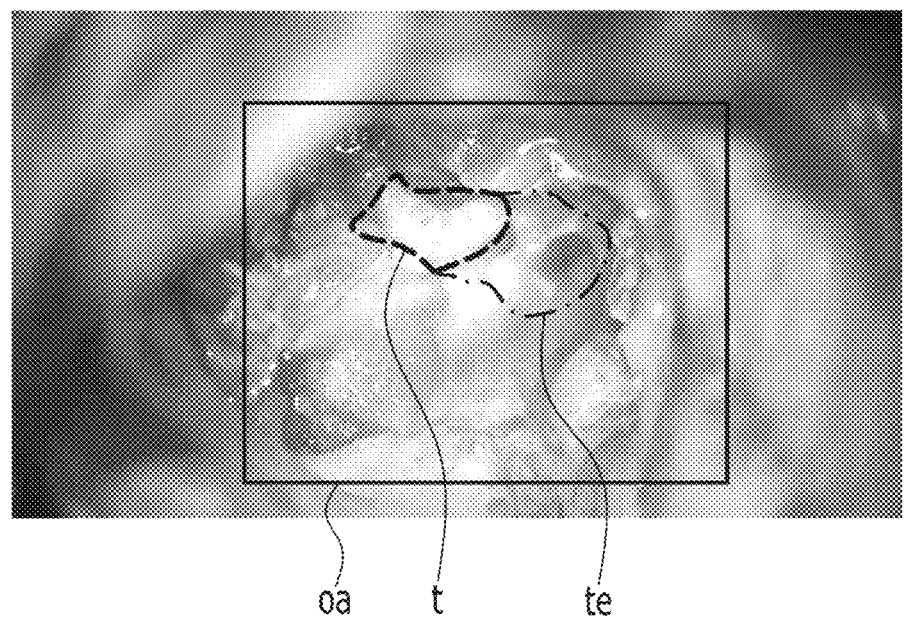

Specifically, referring to FIG. 2, the recognition part (20) recognizes the upper edge of the surgical tool (e.g., the tubular retractor shown in FIG. 2), and recognizes the region of the surgical field including the recognized edge as the first surgical field (a). If the first surgical field (a) disappears from the moving image within a predetermined number of frames (for example, three frames in FIG. 2) or within a predetermined time, the recognition part (20) recognizes the appropriate moving image as the first shaky moving image, and indicates the markers corresponding to the first time code and last time code of the first shaky moving image.

In addition, the recognition part (20) recognizes the edge of the tool end in the moving image, and recognizes it as the second surgical field. Specifically, referring to FIG. 3, the recognition part (20) recognizes the edge of the tool end and senses the end region (ta) composed of the movement path of the end portion during the reference time, and recognizes the field including the end region (ta) as the second surgical field (oa). If the second surgical field (oa) disappears from the moving image within a predetermined number of frames or within a predetermined time, the recognition part (20) recognizes the appropriate moving image as the second shaky moving image, and indicates the markers corresponding to the first time code and last time code of the second shaky moving image.

Further, the recognition part (20) measures the focal distance of the moving image and compares it with the focal distance input to the input part (10), and if the measured focal distance and the input focal distance are not within a predetermined critical range, the recognition part (20) identifies the appropriate moving image as an unfocused moving image and indicates the markers corresponding to the first time code and last time code of the corresponding moving image.

When the ratio of the blood area to tissue area recognized at the second surgical field (oa) exceeds a predetermined first criterion, the recognition part (20) recognizes it as a bleeding event during the first event. Specifically referring to FIG. 4a and FIG. 4b, when the ratio of the blood area (ba) to the tissue area exceeds 50% in the recognized tissue (FIG. 4a), the recognition part (20) recognizes the image in which the ratio of blood area (ba) exceeds 50% as a bleeding event and indicates the markers corresponding to the first time code and the last time code of the moving image.

The recognition part (20) also recognizes the object in the moving image, and recognizes it as a dead spot event in the first event, when the ratio of the area of the recognized object to the area of the second surgical field (oa) is larger than a predetermined second reference value. Specifically, referring to FIG. 5a and FIG. 5b, the recognition part (50) recognizes the hand (b1 and b2) in the moving image, and when the area of the hand (b1) exceeds 50% of the area of the second surgical field (oa), the recognition part (50) recognizes it as a dead spot event, and indicates the markers corresponding to the first time code and the last time code of the corresponding moving image. However, if the area of the hand (b2) is less than 50% of the area of the second surgical field (oa), the corresponding moving image is not recognized as a dead spot event.

The recognition part (20) recognizes an organ and recognizes a moving image in which a part of the recognized organ disappears as the first extraction event of the first event. Specifically, referring to FIG. 6a and FIG. 6b, the recognition part (50) recognizes the Malleus head (t) at the second surgical field (oa). The recognition part (50) recognizes the moving image, in which a part (te) of the Malleus head has disappeared within a predetermined number of frames or a predetermined time after recognizing the Malleus head (t), as the first extraction event, and indicates the markers corresponding to the first time code and the last time code of the corresponding moving image. For convenience of explanation, the Malleus head has been selected as an example of a recognized organ, but the present embodiment is not limited thereto.

In addition, the recognition part (20) recognizes the second event using the result of recognizing the tool in the moving image, and indicates the markers corresponding to the first time code and the last time code of the moving image corresponding to the second event.

Figure 7:
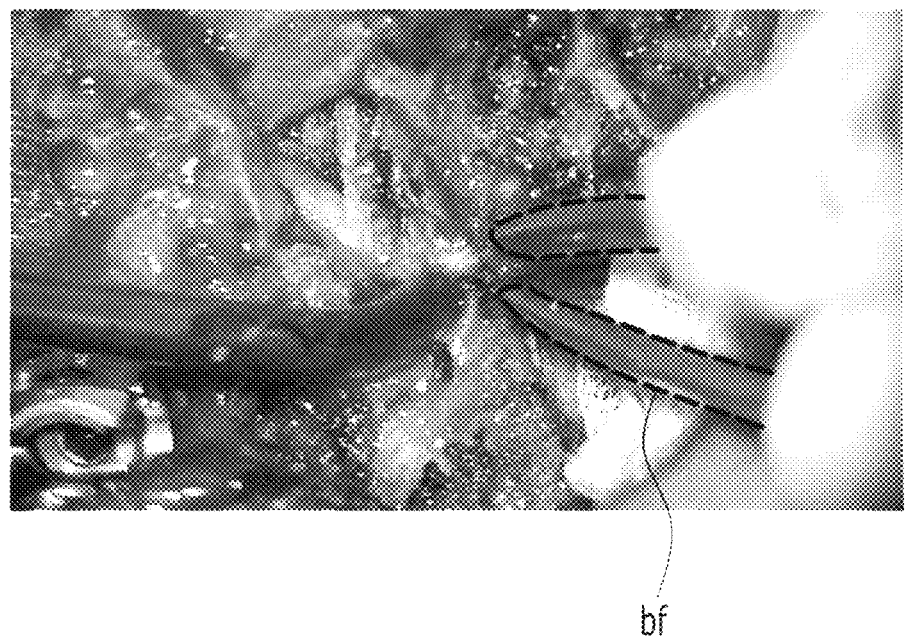
FIG. 7 shows an example in which the image recognition part according to the present embodiment recognizes the hemostatic event.

Specifically, referring to FIG. 7, the recognition part (20) recognizes bipolar forceps (bf) in a moving image, and recognizes the moving image including the bipolar forceps (bf) as a hemostatic event in the second event. The recognition part (20) indicates the markers corresponding to the first time code and the last time code of the image including the bipolar forceps (bf).

Figure 8:
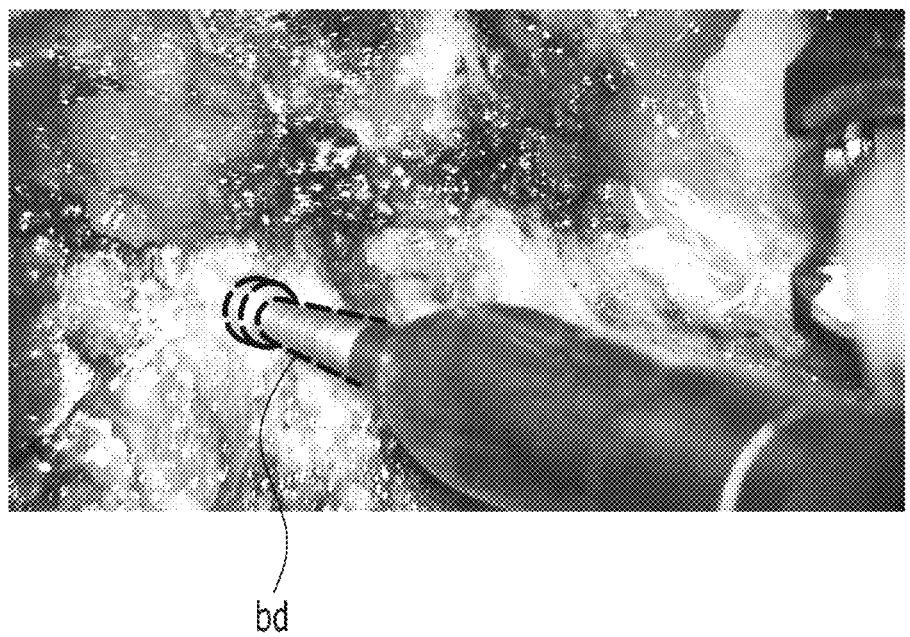
FIG. 8 shows an example in which the image recognition part according to the present embodiment recognizes the drilling event.

Referring to FIG. 8, the recognition part (20) identifies a 3 mm burr drill (bd) in the moving image, and recognizes the moving image including the burr drill (bd) as a drilling event of the second event. The recognition part (20) indicates the markers corresponding to the first time code and the last time code of the image including the burr drill (bd).

Figure 9:
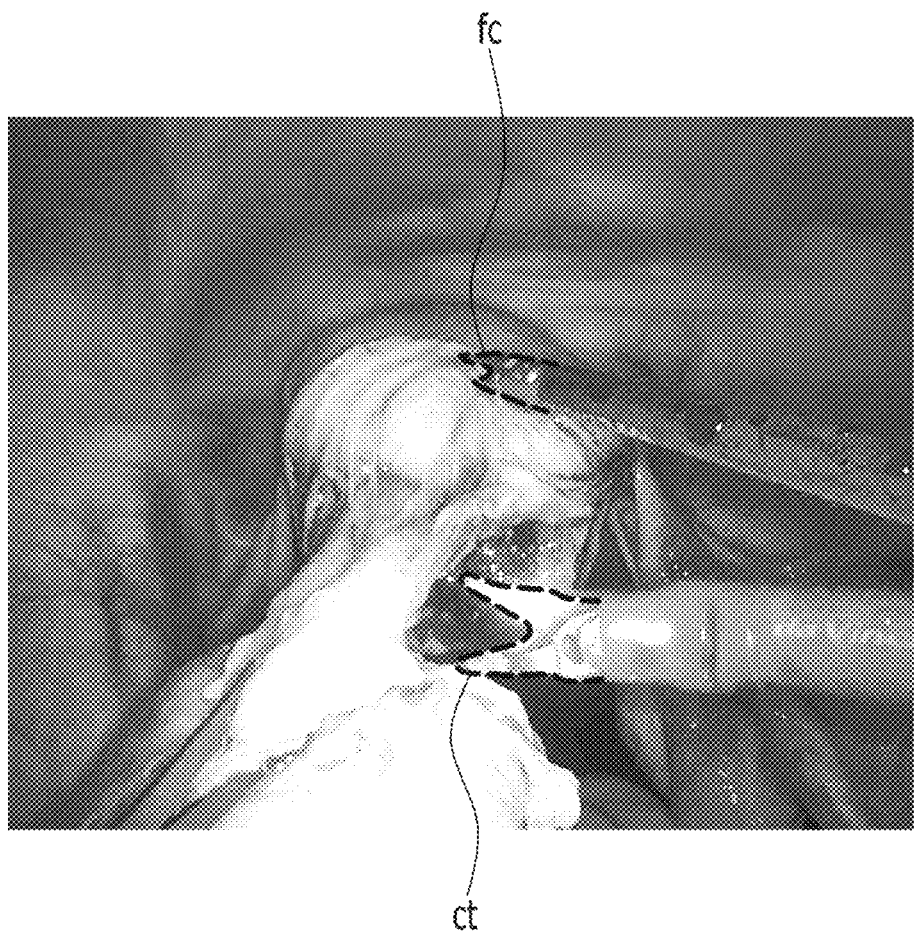
FIG. 9 shows an example in which the image recognition part according to the present embodiment recognizes the second extraction event.

Referring to FIG. 9, the recognition part (20) identifies the forceps (fc) and the cutter (ct) in the moving image, and recognizes the moving image including the forceps (fc) and the cutter (ct) as a second extraction event of the second event. The recognition part (20) indicates the markers corresponding to the first time code and the last time code of the image including the forceps (fc) and the cutter (ct).

Figure 10:
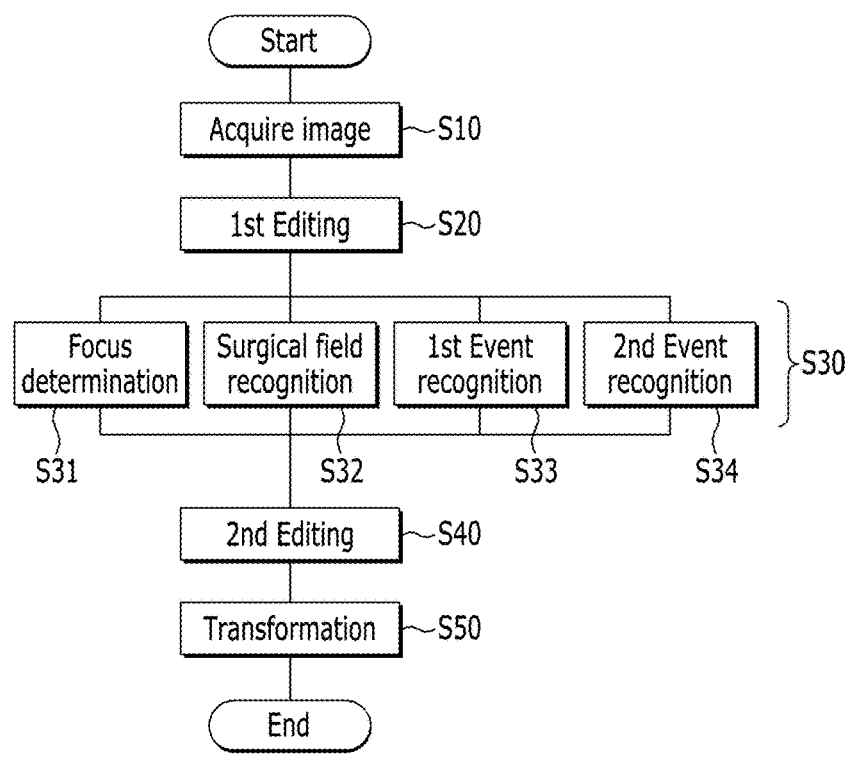
FIG. 10 is a flowchart illustrating the surgical video production method according to the present embodiment.

Hereinafter, the surgical video production method according to the present embodiment of the present invention is explained using FIG. 10.

In step S10, information on the moving image and the focal distance are input to the input part (10).

In step S20, the input part (10) performs the first editing step.

Step S30 includes a plurality of steps S31 to S34. In step S30, the recognition part (20) recognizes the surgical tool, the surgical field, and the object in the moving image, recognizes shaky moving images and unfocused moving images, and recognizes the events (e.g., bleeding, hemostasis, dead spot, and extraction) which occur during surgery.

Specifically, in step S31, the recognition part (20) measures the focal distance of the moving image, and compares it with the focal distance input to the input part (10). If the measured focal distance and the input focal distance are not within a predetermined critical range, the recognition part (20) determines the appropriate moving image as an unfocused moving image and indicates the markers corresponding to the first time code and last time code of the corresponding moving image.

In step S32, the recognition part (20) recognizes the first surgical field and indicates the markers corresponding to the first time code and the last time code of the first moving image using the first surgical field. The recognition part (20) recognizes the second surgical field and indicates the markers corresponding to the first time code and the last time code of the second shaky moving image using the second surgical field.

In step S33, the recognition part (20) recognizes the first event including the bleeding event, the dead spot event, and the first extraction event, and indicates the markers corresponding to the first time code and the last time code of the corresponding moving image.

In step S34, the recognition part (20) recognizes the second event including the hemostatic event, the drilling event, and the second extraction event, and indicates the markers corresponding to the first time code and the last time code of the corresponding moving image.

The steps S31 to S34 are not time series steps, and the recognition part (20) can perform the plurality of steps S31 to S34 at the same time or in any order.

In step 40, the editing part (30) performs the second editing using the markers of the recognition part (20).

In step S50, the transformation part (40) transforms the second editing completed moving image into a 3D stereoscopic image.

Although the present invention has been described in detail in the foregoing, it should be noted that the scope of the present invention is not limited thereto, and a variety of modifications and improvements using the basic concepts in the following claims of the present invention should fall within the scope of this invention. Therefore, the above detailed description should be considered in all respects as illustrative and not restrictive. The scope of the present invention should be determined by rational interpretation of the appended claims, and all changes within the equivalent scope of the present invention should be included in the scope of the present invention.

EXPLANATION OF SYMBOLS

1: System
10: Input part
20: Recognition part
30: Editing part
40: Transformation part

The invention claimed is:

1. A surgical video production system comprising: an input part which records time codes in a moving image photographed by a camera mounted on a surgical microscope, and inputs a focal distance of a lens of the camera and information of surgical tools;
   a recognition part which generates recognition information by recognizing the surgical tools, surgical fields, organs, tissue, and objects in the video image, identifies unfocused video and shaky video among video using the recognition information, indicates markers corresponding to a first time code and a last time code of each of the unfocused video and the shaky video, and indicates the markers corresponding to the first time code and the last time code of the video corresponding to an event by recognizing an event occurring during surgery using the recognition information;
   an editing part which deletes a part of the moving image using the markers or separates a moving image according to the event to generate an edited image; and
   a transformation part which transforms the edited image into a stereoscopic image.

2. The surgical video production system according to claim 1, wherein the recognition information includes an edge of the surgical tool, an edge of the surgical field, an edge of the organ, and an edge of the tissue.

3. The surgical video production system according to claim 2, wherein the recognition part recognizes a region of the surgical field which includes an edge of the surgical tool as a first surgical field, and when the first surgical field disappears within a first time, the appropriate moving image is determined as a first shaky moving image.

4. The surgical video production system according to claim 3, wherein the recognition part recognizes movement of the end of the surgical tool, senses an end region constituted by the movement path of the end during a reference time, and recognizes the field which includes the end region as a second surgical field, and when the second surgical field disappears within a second time, the moving image is recognized as a second shaky moving image.

5. The surgical video production system according to claim 4, wherein the recognition part compares a focal distance measured in the moving image with an input measured distance, and when the measured focal distance and the input focal distance are not within a critical range, the appropriate moving image is identified as the unfocused one.

6. The surgical video production system according to claim 5, wherein the event includes a bleeding event, a blind spot event, a first extraction event, a hemostasis event, a drilling event, and a second extraction event, and the object includes blood,
   and when a ratio of the area of the blood to the area of the tissue at the second surgical field exceeds a first reference value, the recognition part recognizes the corresponding moving image as the bleeding event.

7. The surgical video production system according to claim 6, wherein the object includes a hand,
   and the recognition part recognizes the corresponding motion image as the blind spot event when the area of the hand exceeds a second reference value at the second surgical field.

8. The surgical video production system according to claim 7, wherein the recognition part recognizes a corresponding moving image as the second extraction event, when a part of the recognized organs disappears within a third time.

9. The surgical video production system according to claim 8, wherein the surgical tool includes a bipolar forceps, a burr drill, forceps, and a cutter,
   and the recognition part recognizes the moving image including the bipolar forceps as the hemostatic event, the moving image including the burr drill as the drilling event, and the moving image including the forceps and the cutter as the hemostatic event, respectively.

10. The surgical video production system according to claim 9, wherein the recognition information is generated using a moving image analysis algorithm or a deep learning technique.

11. The surgical video production system according to claim 10, wherein the edge of the surgical tool, the edge of the surgical field, the edge of the organ, and the edge of the tissue are identified using at least one of Sobel, Prewitt, Roberts, Compass, Laplacian, Laplacian of Gaussian (LoG), and Canny methods.

12. The surgical video production system according to claim 11, wherein the transformed stereoscopic image is a stereoscopic surgery moving image for educating surgeons.

\* \* \* \* \*